(12) United States Patent
Crowe et al.

(10) Patent No.: US 9,675,802 B2
(45) Date of Patent: Jun. 13, 2017

(54) METHOD AND APPARATUS FOR STIMULATING THE LOWER BACK AND ABDOMINAL MUSCLES

(75) Inventors: Louis Crowe, Dublin (IE); Brian Caulfield, Dublin (IE); Conor Minogue, County Galway (IE)

(73) Assignees: University College Dublin, National University of Ireland, Dublin, Dublin (IE); Bio-Medical Research Ltd., Galway (IE)

(\*) Notice: Subject to any disclaimer, the term of this patent is extended or adjusted under 35 U.S.C. 154(b) by 0 days.

(21) Appl. No.: 13/382,787

(22) PCT Filed: Jun. 16, 2010

(86) PCT No.: PCT/EP2010/058465
§ 371 (c)(1),
(2), (4) Date: Jan. 6, 2012

(87) PCT Pub. No.: WO2011/003709
PCT Pub. Date: Jan. 13, 2011

(65) Prior Publication Data
US 2012/0116477 A1    May 10, 2012

(30) Foreign Application Priority Data
Jul. 10, 2009    (IE) .................... S2009/0525

(51) Int. Cl.
*A61N 1/36*    (2006.01)
*A61N 1/18*    (2006.01)
*A61N 1/32*    (2006.01)

(52) U.S. Cl.
CPC ......... *A61N 1/36032* (2013.01); *A61N 1/321* (2013.01); *A61N 1/36021* (2013.01)

(58) Field of Classification Search
CPC . A61N 1/18; A61N 1/321; A61N 1/36; A61N 1/36003; A61N 1/36021
USPC ............... 600/382, 390, 393; 607/46, 152
See application file for complete search history.

(56) References Cited

U.S. PATENT DOCUMENTS

| | | | | |
|---|---|---|---|---|
| 2,661,744 A * | 12/1953 | Browner | ................ | 607/149 |
| 2,842,135 A * | 7/1958 | Browner | ................ | 607/3 |
| 4,326,534 A * | 4/1982 | Axelgaard et al. | ........ | 607/43 |
| 4,381,012 A * | 4/1983 | Russek | ................ | 600/382 |
| 4,432,368 A * | 2/1984 | Russek | ................ | 600/382 |

(Continued)

FOREIGN PATENT DOCUMENTS

| | | |
|---|---|---|
| GB | 2 369 998 A | 6/2002 |
| WO | 02/068040 A2 | 9/2002 |
| WO | 2006/061805 A2 | 6/2006 |

*Primary Examiner* — Christopher A Flory
(74) *Attorney, Agent, or Firm* — Nath, Goldberg & Meyer; Jerald L. Meyer

(57) ABSTRACT

A method and apparatus for stimulating the lower back and abdominal muscles in a patient comprising applying a first electrode A1/A2 substantially centrally to the lower lumbar region of the patient's body, and applying second and third electrodes B, C respectively to opposite side flanks of the patient's body. The electrodes are energized to apply a first group of muscular stimulation current pulses which flow between the second and third electrodes and a second group of muscular stimulation current pulses which flow between the first electrode and the second and third electrodes alternately.

15 Claims, 3 Drawing Sheets

(56) References Cited

U.S. PATENT DOCUMENTS

| | | | |
|---|---|---|---|
| 4,498,480 A * | 2/1985 | Mortensen | 600/383 |
| 4,832,033 A * | 5/1989 | Maher et al. | 607/48 |
| 4,871,439 A * | 10/1989 | Enzer et al. | 204/401 |
| 4,971,069 A * | 11/1990 | Gracovetsky | 600/594 |
| 5,022,412 A * | 6/1991 | Gracovetsky et al. | 600/382 |
| 5,443,494 A * | 8/1995 | Paolizzi et al. | 607/149 |
| 6,065,154 A * | 5/2000 | Hulings et al. | 2/102 |
| 6,137,675 A * | 10/2000 | Perkins | 361/679.03 |
| 6,546,290 B1 * | 4/2003 | Shloznikov | 607/48 |
| 6,728,577 B2 * | 4/2004 | Minogue et al. | 607/48 |
| 6,760,629 B2 * | 7/2004 | Minogue et al. | 607/149 |
| 6,885,896 B2 * | 4/2005 | Minogue et al. | 607/48 |
| 7,022,093 B2 * | 4/2006 | Smith et al. | 602/2 |
| 7,069,089 B2 * | 6/2006 | Minogue et al. | 607/149 |
| 7,580,753 B2 * | 8/2009 | Kim | A61N 1/0558 607/46 |
| 7,610,096 B2 * | 10/2009 | McDonald, III | A61H 39/002 607/117 |
| 7,747,327 B2 * | 6/2010 | Minogue et al. | 607/48 |
| 7,797,039 B2 * | 9/2010 | Koivumaa et al. | 600/521 |
| 7,991,477 B2 * | 8/2011 | McDonald, III | A61H 39/002 607/117 |
| 8,473,064 B2 * | 6/2013 | Castel | A61N 1/0452 607/48 |
| 2002/0058972 A1 * | 5/2002 | Minogue et al. | 607/72 |
| 2002/0077688 A1 | 6/2002 | Kirkland | |
| 2002/0133195 A1 * | 9/2002 | Minogue et al. | 607/2 |
| 2002/0165590 A1 * | 11/2002 | Crowe et al. | 607/48 |
| 2004/0054276 A1 * | 3/2004 | Finneran et al. | 600/393 |
| 2004/0127954 A1 * | 7/2004 | McDonald, III | 607/48 |
| 2004/0215285 A1 * | 10/2004 | Pollock | 607/46 |
| 2005/0187071 A1 * | 8/2005 | Yamashita et al. | 482/1 |
| 2007/0049814 A1 * | 3/2007 | Muccio | 600/388 |
| 2007/0118032 A1 * | 5/2007 | Finneran et al. | 600/393 |
| 2007/0293911 A1 * | 12/2007 | Crowe et al. | 607/48 |
| 2008/0097530 A1 * | 4/2008 | Muccio et al. | 607/3 |
| 2008/0147143 A1 * | 6/2008 | Popovic et al. | 607/48 |
| 2009/0036888 A1 * | 2/2009 | Dunfee et al. | 606/54 |
| 2009/0118789 A1 * | 5/2009 | Buhlmann et al. | 607/46 |
| 2009/0319003 A1 * | 12/2009 | Castel et al. | 607/48 |
| 2010/0174250 A1 * | 7/2010 | Hu | A61F 5/4401 604/319 |
| 2011/0276108 A1 * | 11/2011 | Crowe et al. | 607/48 |
| 2012/0116477 A1 * | 5/2012 | Crowe et al. | 607/46 |
| 2012/0144551 A1 * | 6/2012 | Guldalian | 2/102 |
| 2012/0238923 A1 * | 9/2012 | Yamashita | A41D 13/1236 601/46 |
| 2013/0144231 A1 * | 6/2013 | Hu | A61F 5/4401 604/319 |
| 2014/0005745 A1 * | 1/2014 | Castel et al. | 607/48 |
| 2014/0005759 A1 * | 1/2014 | Fahey | A61F 7/10 607/99 |
| 2016/0022481 A1 * | 1/2016 | Fahey | A61F 7/10 607/3 |
| 2016/0184140 A1 * | 6/2016 | Hu | A61F 5/4401 602/52 |

* cited by examiner

METHOD AND APPARATUS FOR STIMULATING THE LOWER BACK AND ABDOMINAL MUSCLES

This is a National Phase Application filed under 35 U.S.C. §371 as a national stage of International Application No. PCT/EP2010/058465, filed Jun. 16, 2010, claiming the benefit from Irish Patent Application No. S2009/0525, filed Jul. 10, 2009, the entire content of each of which is hereby incorporated by reference in its entirety.

This invention relates to a method and apparatus for stimulating the lower back and abdominal muscles in a patient.

BACKGROUND

Non-pathological lower back pain, i.e., back pain associated with weakness, inhibition, wasting, misfiring/mistiming or abnormalities of the muscles that support the trunk rather than secondary to cancer, infection, fractures, etc., is a leading cause of morbidity, sick leave and physician consultations.

Contributory factors include inhibition of muscle activity (perhaps secondary to the pain itself), inability of the patient to voluntarily control the specific muscles and appropriately perform rehabilitation exercises, and lack of compliance with the exercise regimes.

These muscles include multifidus, the obliques and transversus abdominis. It is thought that the deep fibres of multifidus are especially important in stabilising the spine. These muscle fibres have been historically difficult to recruit and train through traditional techniques including the following:

(a) Voluntary exercises (with or without equipment).

These are difficult to do properly, especially without the attendance of (expensive) trained personnel. The muscle itself may not be properly recruited. Compliance may be poor. Results are variable.

(b) Transcutaneous electrical nerve stimulation (TENS).

TENS is a form of symptomatic relief. The hope is that with reduced pain the muscle may begin to function normally again alleviating the on-going pain. Studies suggest that the a third of people get substantial relief, a third improve somewhat and the remaining get little benefit.

(c) Implanted stimulation techniques.

These are, by their nature, invasive and have not been shown to have clear benefit beyond other techniques for a typical patient.

(d) Neuromuscular electrical stimulation (NMES).

NMES has been around for many decades. It is not routinely used in the treatment of lower back pain because it has not been shown to have therapeutic benefits beyond TENS. The NMES used tends to cause contraction of relatively superficial muscle fibres of the lower back and not target the deep muscle fibres where a lot of the supporting and stabilisation of the back is thought to occur. Usually the current travels between pads placed on the lower back. Because the current is substantially travelling through one plane, i.e. in line with the skin, the current tends not to travel deeply at the intensities required to stimulate deep fibres.

In addition because it is uncomfortable to selectively stimulate the lower back (in comparative isolation) the contractions tend to be painful and may cause hyperextension of the lower back. This limits the current intensity thus the likelihood of direct stimulation of the deep paraspinal fibres is less likely. The abdominal musculature tends to be less activated, hence receives less training and the inner fibres supporting the spine remain comparatively inactive.

Additionally, although the pulses and pad positions may be balanced with traditional NMES, the resulting muscle contraction may be imbalanced. This may be due to greater muscle weakness on one side—a common finding in lower back pain. This may cause potentially harmful skewing of the patient.

U.S. Pat. No. 4,381,012, Russek discloses a TENS belt with electrodes located close to the spine and electrodes more lateral to the spine. However, Russek is not an effective lower back pain treatment, nor an advance on standard therapies, merely away to apply standard therapies. The suggested positions are for TENS and the use of the set up at a user tolerable and safe level would not elicit contractions of the deep multifidus fibres.

The high prevalence of chronic lower back pain suggests that the current therapeutic approaches are insufficient in some way. It is an object of the invention to provide an improved method and apparatus for treating lower back pain.

SUMMARY OF THE INVENTION

According to the present invention there is provided a method of stimulating the lower back and abdominal muscles in a patient, comprising applying a first electrode to the lower lumbar region of the patient's body, applying second and third electrodes respectively to opposite side flanks of the patient's body, and energising the electrodes to apply a first group of muscular stimulation current pulses which flow between the second and third electrodes and a second group of muscular stimulation current pulses which flow between the first electrode and the second and third electrodes.

Preferably the first electrode extends between and covers at least the upper sacrum and the fifth lumber vertebra of the patient. Most preferably the lower end of the first electrode forms a wedge shape which points into the patient's gluteal cleft.

The first electrode may comprise two individually energisable segments disposed substantially symmetrically relative to the patient's spine.

Preferably each of the second and third electrodes is located between the patient's iliac crest and ribs. At least one of the second and third electrodes may comprise a plurality of individually energisable segments.

In a preferred embodiment the electrodes are incorporated in a garment which locates the electrodes at desired positions against the patient's skin.

The invention further provides an apparatus for stimulating the lower back and abdominal muscles in a patient, comprising a first electrode for application to the lower lumbar region of the patient's body, second and third electrodes for application respectively to opposite side flanks of the patient's body, and drive circuitry arranged to energise the electrodes to apply a first group of muscular stimulation current pulses which flow between the second and third electrodes and a second group of muscular stimulation current pulses which flow between the first electrode and the second and third electrodes.

Preferably the electrodes are incorporated in a garment which locates the electrodes at desired positions against the patient's skin.

BRIEF DESCRIPTION OF THE DRAWINGS

An embodiment of the invention will now be described, by way of example, with reference to the accompanying drawings, in which.

DESCRIPTION OF THE PREFERRED EMBODIMENT

Figure 1:
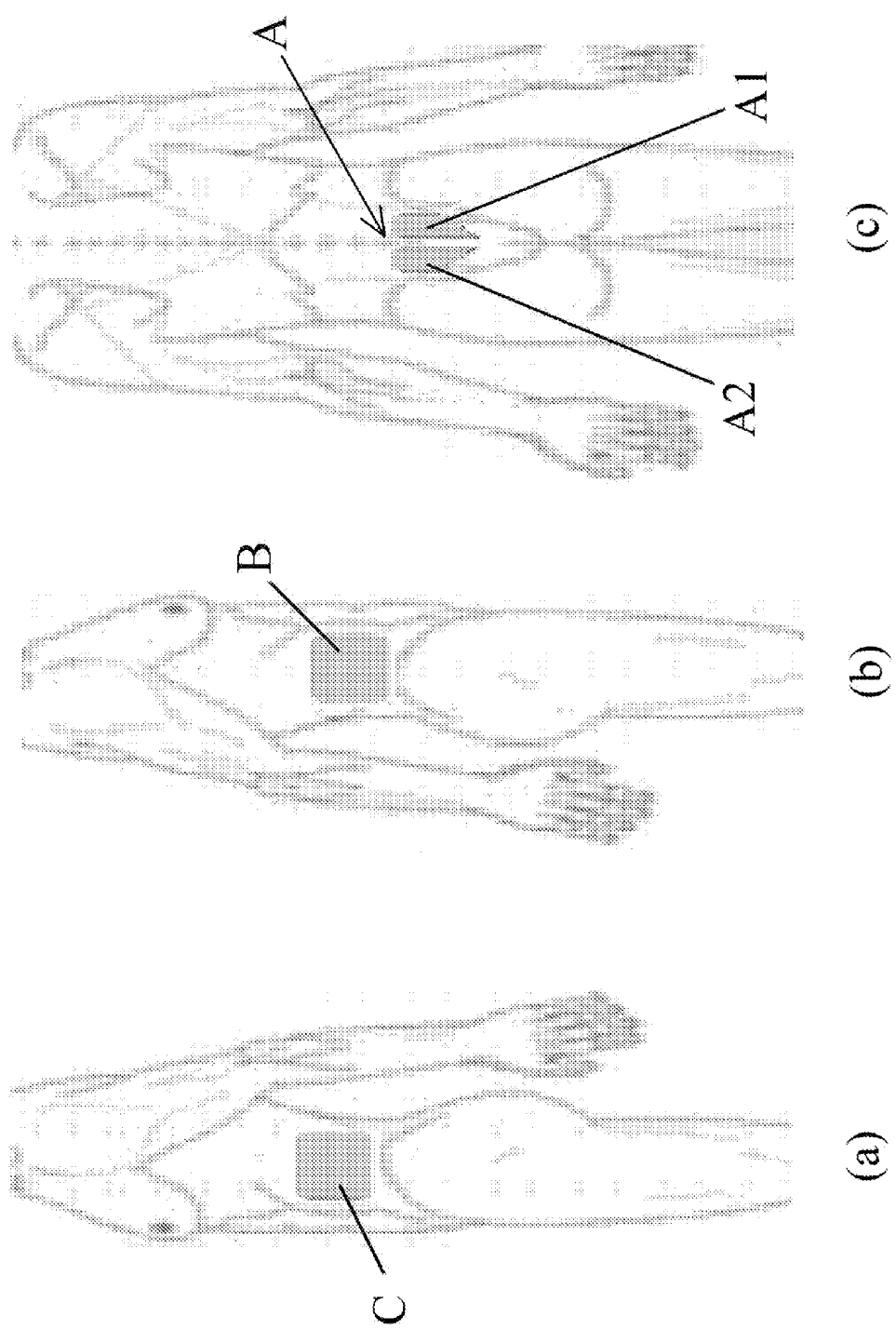
FIGS. 1(a) to 1(c) are schematic views of, respectively, the left-hand side, the right-hand side and the back of a patient wearing a set of electrodes according to the embodiment.

Referring to FIG. 1, in the embodiment a method of stimulating the lower back and abdominal muscles in a patient comprises applying a set of large-area electrodes A to C externally to the patient's body in the lumbar region. The electrodes are disposed on the patient's skin at least approximately symmetrically relative to the patient's midline (dashed vertical line in FIG. 1(c), which also represents the spine).

Electrode A, comprising two mutually insulated segments A1 and A2, is positioned on the lower back. Electrodes B and C are positioned on the right and left sides respectively. Electrode segments A1 and A2 each have an approximate length of 10 cm, an approximate width of 5 cm, and an approximate area of 25 cm$^2$. Electrodes B and C are rectangular and each is approximately 180 cm$^2$ in area (each has approximate dimensions 12 cm×15 cm). Each of electrodes B and C has an area approximately 3-4 times the area of the electrode A (i.e. the combined area of segments A1 and A2). This ratio has been found to give comfortable balanced stimulation in healthy people with a single pulse going from C to AB or D to AB, as will be described. In general it is preferred that the electrode A have an area less than half that of the electrode B or C.

Electrode segments A1 and A2 are vertically aligned and adjacent to each other, substantially symmetrical to the patient's spine. As used herein, expressions of orientation such as "vertical" and "horizontal" refer to the patient when standing. A small gap of, say, a few millimeters between electrode segments A1 and A2 has been found to be adequate. This gap between the segments aids in the placement of the electrode A as a patient can easily palpate the vertical gap acting as a check that the electrode is properly aligned on the back. (The spinous processes of the vertebrae are easily felt too). A ridge on a backing for these electrodes or on an application garment (FIG. 2) may also facilitate proper positioning and orientation of the electrode A. The optimal gap will depend on many factors including the set of electrodes and in particular the electrical and mechanical properties of the electrode gel, if used.

Overall the lower end of the electrode A, i.e. the two segments A1, A2 together, forms a wedge shape. This shape conforms well to the lower back. The wedge points straight down into the gluteal cleft (this also aids proper orientation and positioning). The lower part of the electrode A extends just over the upper sacrum. The wedge shape means that it is not directly over the gluteal muscles. In particular it lies up from (i.e., away from) the upper edge of gluteus medius which arches up and lateral from the sacrum.

The height (vertical length) of the electrode A is such that it extends between and covers at least the fifth lumbar vertebra and the upper sacrum, and preferably the fourth and fifth lumbar vertebrae. Lumbar vertebrae 4 and 5 are the most typical sites of muscle wasting associated with lower back pain. This height limitation means that the current is less likely to recruit large amounts of erector spinae muscle the fleshy part of which becomes progressively more prominent above lumbar vertebra 4. At a physician's discretion the electrode A may be positioned further up to more directly target wasting if it is situated superiorly. The width of electrode A approximates the width of multifidus and the vertebra.

If desired, electrode segments A1 and A2 may be joined to form one single electrode A. As discrete segments, however, they allow greater left-right balancing of the muscle contractions, as described below.

Electrodes B and C are positioned on the person's opposite side flanks between the iliac crest and the ribs. As with the lower back electrode A, these are positioned in relation to bony points. This ensures accurate and repeatable positioning of the electrodes.

Connection wires (not shown) are connected individually to the electrodes B, C and electrode segments A1, A2 which allow muscular stimulation current pulses to be applied to the patient.

Although the electrodes may be attached at their desired positions individually to the patient's skin, e.g. using hydrogel, it is preferred that they are incorporated in a pre-wired garment which locates the electrodes more reliably at the desired positions and which prevents inadvertent miswiring of the electrodes.

Figure 2:
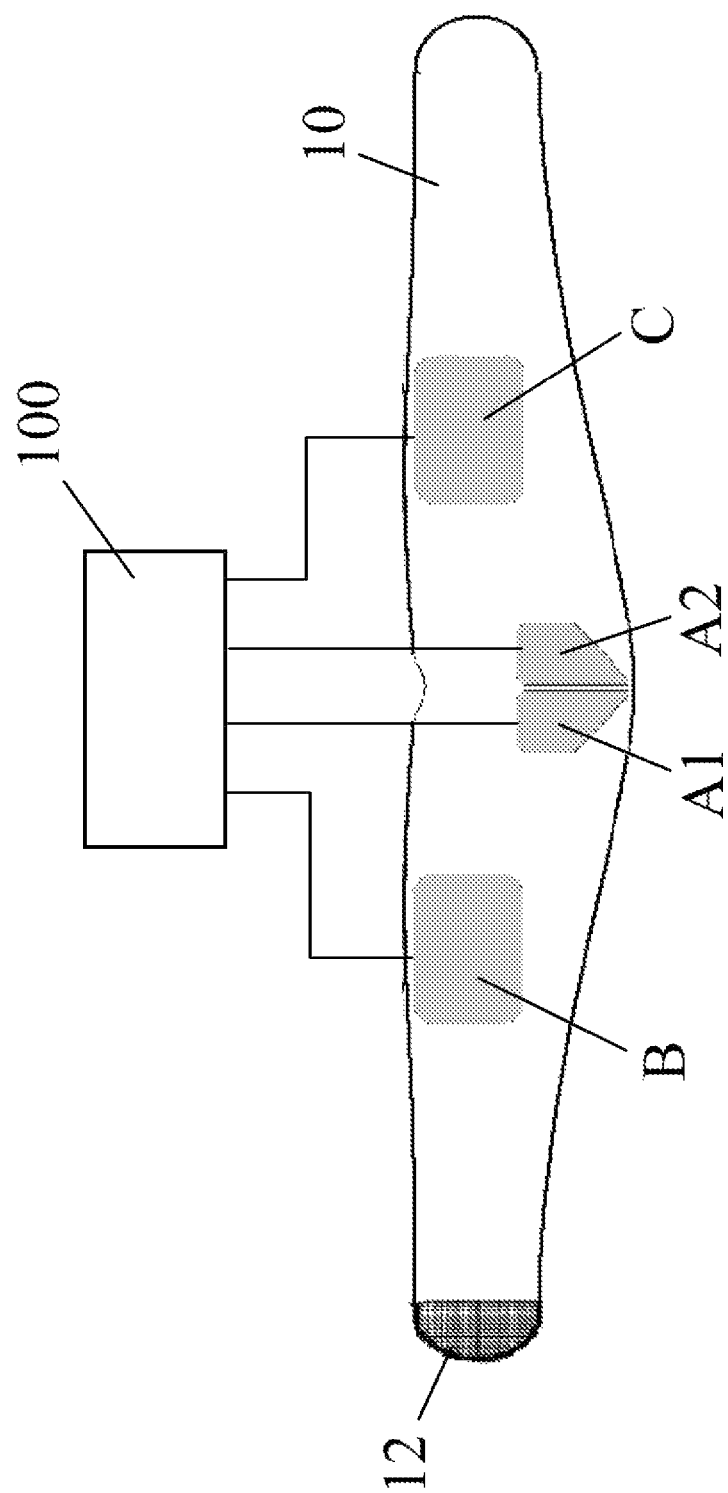
FIG. 2 is a plan view of a garment incorporating the electrodes of FIG. 1.

An example is shown in FIG. 2, which is a plan view of the inside surface of a wide belt-like wrap 10 for fitting around the patient's midriff. In use the wrap 10 is wrapped around the patient's waist region with the electrodes on the inside, so that the electrodes A1, A2, B and C bear against the patient's skin at the appropriate locations on the patient's body. All or selected parts of the wrap may be elasticated so that the wrap is stretched around the region for snug fitting. Having areas of differing stretchability allows for a better fit. The wrap 10 is secured in place by Velcro hooks 12 at one end which engage a region of Velcro loops (not shown) at the other end.

Wiring (not shown) to the electrodes is integrated into the wrap 10; techniques are known to do this. The electrodes may be pre-fixed to the wrap at manufacture, or they may be fixed by the user at pre-printed locations on the wrap. In the latter case the wiring for each electrode terminates in an exposed stud in the centre of the electrode area. Adhesive electrodes are then placed onto the wrap in the designated areas. One side of the electrode sticks to the inner surface of the wrap and the other bears against the skin when the wrap is worn. The wiring allows each electrode to be individually energised if desired.

To reduce the number of wrap sizes required, the printing of the electrode positions may be different for small/medium/large body sizes.

The material of the wrap may be resiliently deformable, such as neoprene. To avoid separation of the electrodes from the wrap 10 when the wrap is stretched around a subject, the wrap may comprise an inelastic material in the electrode regions.

Of course, using an expanded belt-type garment is merely one of many apparels that would allow easy and correct electrode placement. Additional nick, folds etc., on the apparel may aid correct placement. This is particularly important for the correct placement of the back electrodes as they cannot be easily visualised. Additionally when adhesive electrodes are used they are harder to reposition. As has been used in TENS of the lower back, extra cushioning/padding in the lower back may help keep the electrodes opposed to the skin—more important if non-adhesive electrodes are used.

In FIG. 2 the drive circuitry 100 is also schematically illustrated, and this may be constructed according to principles well-known in the NMES field. PCT/IB02/03309 discloses an electronic controller which can select electrodes from an array of electrodes to create current paths in the body.

In the preferred embodiment, the current pulses applied to the electrodes are divided into two groups, the duration and intensity of which may be independently controlled.

Figure 3:
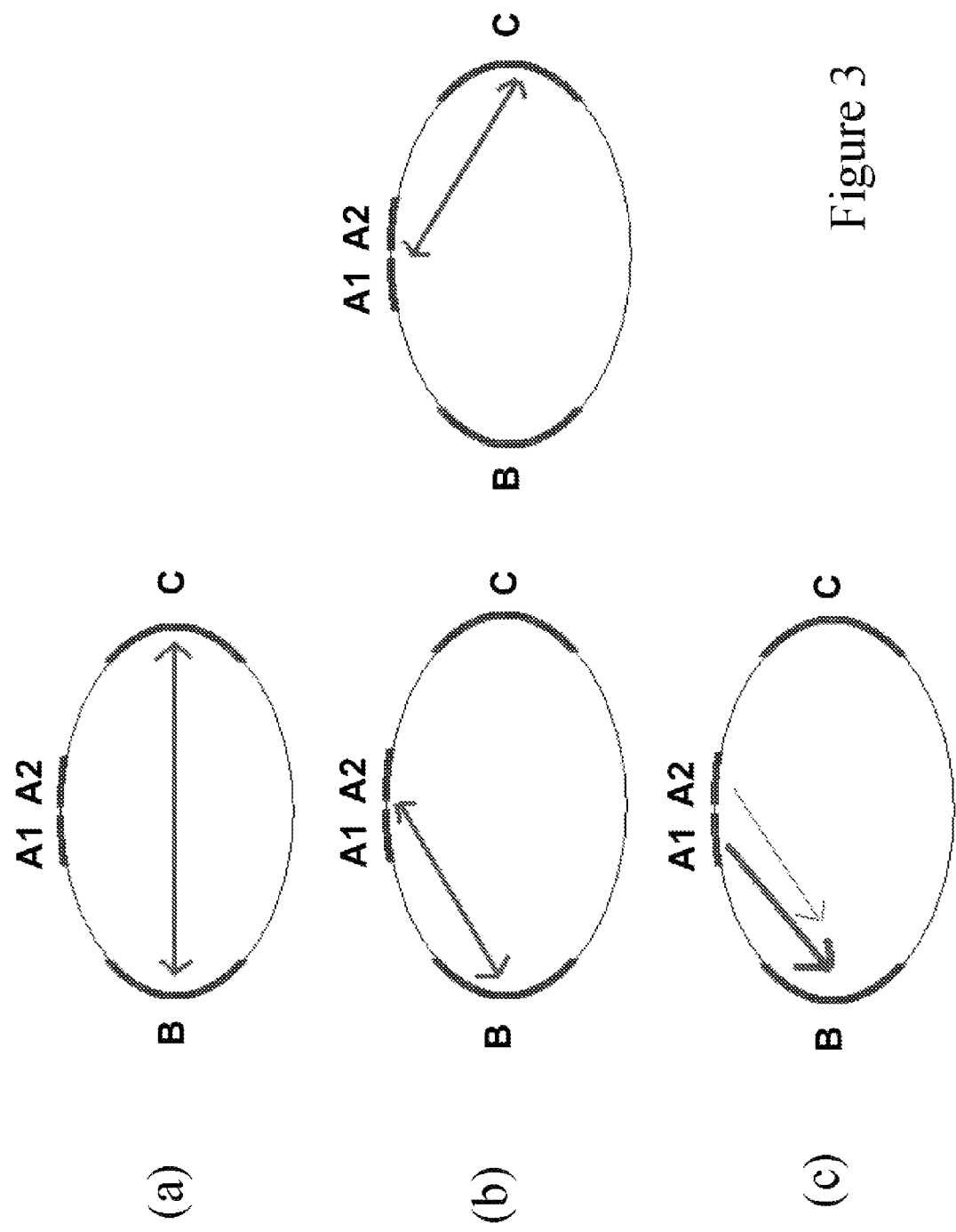
FIGS. 3(a) to 3(c) are schematic diagrams representing a cross-section through a patient's lumbar region showing the paths of treatment pulses.

Group 1 pulses travel between electrodes B and C, FIG. 3(a), and may be thought of as stimulating primarily the abdominal muscles. The frequency of Group 1 pulses is 30 Hz. Successive Group 1 pulses travel alternately in opposite directions between the electrodes B and C, i.e. B→C, C→B, B→C, etc.

Group 2 pulses travel between electrode A (segments A1 and A2 considered as a single electrode) and electrodes B and C alternately. Group 2 pulses are sub-divided into successive sets of four pulses. In each set the first two pulses are at 50% of the intensity of the last two pulses. In each set of four pulses the first pulse travels from electrode A to electrode B, the second pulse travels from electrode A to electrode C, the third pulse travels from electrode A to electrode B and the fourth pulse travels from electrode A to electrode C. Each Group 2 pulse follows the previous pulse after a 10 ms delay. The frequency of the sets of four pulses is 20 Hz, i.e., there are 80 discrete Group 2 pulses per second.

In both Groups 1 and 2 the pulse width=480 us.

The Group 1 and Group 2 pulses are not applied continuously to the electrodes. Rather, the pulses in each group are applied during successive therapy (contraction) periods alternating with relaxation periods where no pulses of that group are applied. Typically, the pulses of each group are applied cyclically with the following contraction-relaxation characteristics in each cycle:

Ramp-Up=0.50 sec (pulses at increasing intensity)
Contraction Period=4.00 sec (pulses at maximum intensity)
Ramp-Down=1.00 sec (pulses at decreasing intensity)
Relax=3.00 sec (no pulses)

Group 1 pulses stabilise and support the trunk and mask the contraction of Group 2 pulses. For this reason it is preferred that the periods during which the Group 1 pulses are applied are at least temporally co-extensive with the periods during which the Group 2 pulses are applied. With the contraction-relaxation cycle shown above the support muscles of the trunk tend to start contracting appreciably first, due to the selected pulse parameters, frequencies and the neuroanatomy of the region.

It should be noted that individual intensity control of Group 1 and Group 2 pulses allows an individual to find the relative intensities that suit him best. This may vary with absolute intensity and as the patient progresses with treatment. Typically, the current levels which have been shown to be satisfactory are 50 mA in the A-B and A-C paths, and 70 mA in the B-C path.

A balanced pulse and set-up may cause an imbalanced muscle contraction. By way of example, suppose a patient has a weakness in his right lower back (on the side of electrode segment A1). Similar current though electrode segments A1 and A2 may cause a stronger contraction in his left lower back, putting a skewing strain towards his left. To counteract this, pulses in Group 2 may be adjusted to give a more balanced contraction. In this case for one or more Group 2 pulses the current through electrode segment A1 is set greater than through A2, FIG. 3(c). This may be due to pulses through segment A1 being of a longer pulse duration than through A2 and/or at a relatively higher intensity. Alternatively, current could be passed through only one of the segments A1, A2.

Another example of using unbalanced pulses to give a balanced contraction is to reduce the truncal contractions in the region of electrode B, say, by spreading Group 1 pulses in the area of electrode B. Group 1 pulses normally travel between electrodes B and C. However, by having the current pass between, say, electrode C and electrodes B and A for a portion of the pulse period the relative contraction at B is reduced.

There are many permutations that can lead to appropriately imbalanced pulses. We found that ten permutations varying the imbalance from one side to the other were sufficient to bring about balanced contractions in most patients. The patient simply cycled through the various pre-programmed options and chose the one that gave the best contractions for them. This was noted to vary. As patients progressed with treatment, they tended towards more symmetrical patterns.

In other embodiments, not shown, the electrodes C and D are divided into two or more segments C1, C2, etc. Each segment is individually addressable (electrically energisable) so that separate current pathways, for example A1 to C1, A2 to C2, A1 to B2, etc, may be established. Since such segments C1, C2 are located at different angles with respect to electrode segments A1 and A2, the current path adjacent to the spine may be altered by energising different segments, or sets of segments, of electrodes A, B and C. For each electrode B or C, for one or more Group 1 or Group 2 pulses currents of different intensity and/or duration could be passed simultaneously through more than one segment, or a current could be passed through only one segment.

The embodiments of the invention provide an apparatus and method for comfortably stimulating and effectively training and or re-educating the muscles of the lower back and abdomen. These muscles are important in both the prevention and treatment of back pain. The deep paraspinal fibres of multifidus muscle are thought to be particularly important and, until this invention, difficult to train. The effectiveness is based on the specific size, arrangement and anatomical location of the stimulating electrodes as well as the way in which pulses are passed between the electrodes to elicit targeted muscle contractions.

The invention is not limited to the embodiment described herein which may be modified or varied without departing from the scope of the invention.

The invention claimed is:

1. An apparatus for stimulating muscles in a patient, the apparatus comprising:
   a garment incorporating a plurality of electrodes for application to the patient's body, and drive circuitry arranged to energise the electrodes with current pulses, wherein the apparatus is designed for stimulating the lower back and abdominal muscles of the patient, the electrodes being positioned relative to the garment such that when the garment is worn a first electrode is configured to be located to the lower lumbar region of the patient's body and second and third electrodes are configured to be located respectively to opposite side flanks of the patient's trunk,
   wherein the drive circuitry is configured to apply a first group of muscular stimulation current pulses which flow between the second and third electrodes for stimulating primarily the abdominal muscles; pulses of the first group travel alternately in opposite directions between the second and third electrodes, and a second group of muscular stimulation current pulses which flow between the first electrode and the second and third electrodes, and wherein the first electrode comprises two individually energisable segments with a vertical gap therebetween which is configured to be aligned with the patient's spine when the garment is worn thereby locating the respective segments at opposite sides of the patient's midline;

a lower end of a lateral-most edge of each segment is angled medially and downward so that the first electrode forms a wedge shape which points into the patient's gluteal cleft, thereby avoiding overlaying the gluteal muscles, the two individually energisable segments being configured to be spaced at the midline and overlying at least the upper sacrum and being configured to be located to an area superior to the gluteal cleft in order to minimise overlap with the gluteal muscles such that the multifidus are stimulated, wherein the respective individually energisable segments are selectively activated such that the activated individually energisable segment co-operates with one of the second and third electrodes to define an active current path penetrating the body therebetween along which the second group of muscular stimulation current pulses flows;

the vertical height of the first electrode is limited such that it extends between and covers at least the fifth lumbar vertebra and the upper sacrum of the patient so that current is less likely to recruit large amounts of erector spinae muscle, and the width of the first electrode approximates the width of the multifidus and the vertebra, wherein the area of the first electrode is less than half the area of either second or third electrode to ensure the current density at multifidus is higher than at the second and third electrodes during the second group of muscular stimulation current pulses.

2. The apparatus claimed in claim 1, wherein each of the second and third electrodes are configured to be located between the patient's iliac crest and ribs when the garment is worn.

3. The apparatus claimed in claim 1, wherein at least one of the second and third electrodes comprises a plurality of individually energisable segments.

4. The apparatus claimed in claim 1, wherein the drive circuitry allows a user to select from a number of pre-programmed pulse characteristics, some of which may be asymmetrical in order to achieve a symmetrical contraction.

5. A method of stimulating the lower back and abdominal muscles in a patient, comprising:

applying a first electrode to the lower lumbar region of the patient's body, applying second and third electrodes respectively to opposite side flanks of the patient's trunk, and energising the electrodes to apply a first group of muscular stimulation current pulses which flow between the second and third electrodes for stimulating primarily the abdominal muscles;

pulses of the first group travel alternately in opposite directions between the second and third electrodes; and a second group of muscular stimulation current pulses which flow between the first electrode and the second and third electrodes, wherein the first electrode comprises two individually energisable segments with a vertical gap therebetween which is aligned with the patient's spine thereby locating the respective segments at opposite sides of the patient's midline, a lower end of a lateral-most edge of each segment is angled medially and downward so that the first electrode forms a wedge shape which points into the patient's gluteal cleft, thereby avoiding overlaying the gluteal muscles, the two individually energisable segments being configured to be spaced at the midline and overlying at least the upper sacrum and being configured to be located to an area superior to the gluteal cleft in order to minimise overlap with the gluteal muscles such that the multifidus are stimulated;

wherein the respective individually energisable segments are selectively activated such that the activated individually energisable segment co-operates with one of the second and third electrodes to define an active current path penetrating the body therebetween along which the second group of muscular stimulation current pulses flows;

the vertical height of the first electrode is limited such that it extends between and covers at least the fifth lumbar vertebra and the upper sacrum of the patient such that current is less likely to recruit large amounts of erector spinae muscle, and the width of the first electrode approximates the width of the multifidus and the vertebra, wherein the area of the first electrode is less than half the area of either second or third electrode to ensure the current density at multifidus is higher than at the second and third electrodes during the second group of muscular stimulation current pulses.

6. The method claimed in claim 5, wherein at least some of the pulses in the second group comprise currents of different intensity and/or duration passed through the two segments.

7. The method claimed in claim 5, wherein at least some of the pulses in the second group comprise a current passed through only one of the two segments.

8. The method claimed in claim 5, wherein each of the second and third electrodes is located between the patient's iliac crest and ribs.

9. The method claimed in claim 5, wherein at least one of the second and third electrodes comprises a plurality of individually energisable segments.

10. The method claimed in claim 9, wherein at least some of the pulses in the first group comprise currents of different intensity and/or duration passed through more than one segment of the second and/or third electrode.

11. The method claimed in claim 9, wherein at least some of the pulses in the first group comprise a current passed through only one segment of the second and/or third electrode.

12. The method claimed in claim 5, wherein each of the first and second groups of pulses is applied cyclically, with periods of pulse application alternating with periods when no pulses are applied.

13. The method claimed in claim 5, wherein the electrodes are incorporated in a garment which locates the electrodes at desired positions against the patient's skin.

14. Apparatus for stimulating muscles in a patient, the apparatus comprising:

a garment incorporating a plurality of electrodes for application to the patient's body, and drive circuitry arranged to energise the electrodes with current pulses, wherein the apparatus is designed for stimulating the lower back and abdominal muscles of the patient, the electrodes being positioned relative to the garment such that when the garment is worn a first electrode is configured to be located to the lower lumbar region of the patient's body and second and third electrodes are configured to be located respectively to opposite side flanks of the patient's trunk, wherein the drive circuitry is configured to apply a first group of muscular stimulation current pulses which flow between the second and third electrodes for stimulating primarily the abdominal muscles, wherein pulses of the first group travel alternately in opposite directions between the second and third electrodes, a second group of muscular stimulation current pulses which flow between the first electrode and the second and third electrodes alternately, the first group of pulses are applied at least temporally co-extensive with periods during which the second group are applied so that the first group of pulses mask the contraction of the second group of pulses, and wherein the first electrode comprises two individually energisable segments with a vertical gap therebetween which is configured to be aligned with the patient's spine when the garment is worn thereby locating the respective segments at opposite sides of the patient's midline, wherein a lower end of a lateral-most edge of each segment is angled medially and downward so that the first electrode forms a wedge shape which points into the patient's gluteal cleft, thereby avoiding overlaying the gluteal muscles, the two individually energisable segments being configured to be spaced at the midline and overlying at least the upper sacrum and being configured to be located to an area superior to the gluteal cleft in order to minimise overlap with the gluteal muscles such that the multifidus are stimulated, the vertical height of the first electrode is limited such that it extends between and covers at least the fifth lumbar vertebra and the upper sacrum of the patient so that current is less likely to recruit large amounts of erector spinae muscle, and the width of the first electrode approximates the width of the multifidus and the vertebra, wherein the area of the first electrode is less than half the area of either second or third electrode to ensure the current density at multifidus is higher than at the second and third electrodes during the second group of muscular stimulation current pulses.

15. A method of stimulating the lower back and abdominal muscles in a patient, comprising:

applying a first electrode to the lower lumbar region of the patient's body;

applying second and third electrodes respectively to opposite side flanks of the patient's trunk; and energising the electrodes to apply a first group of muscular stimulation current pulses which flow between the second and third electrodes for stimulating primarily the abdominal muscles;

wherein pulses of the first group travel alternately in opposite directions between the second and third electrodes, a second group of muscular stimulation current pulses which flow between the first electrode and the second and third electrodes alternately, the first group of pulses are applied at least temporally co-extensive with periods during which the second group are applied so that the first group of pulses mask the contraction of the second group of pulses, wherein the first electrode comprises two individually energisable segments with a vertical gap therebetween which is aligned with the patient's spine thereby locating the respective segments at opposite sides of the patient's midline, a lower end of a lateral-most edge of each segment is angled medially and downward so that the first electrode forms a wedge shape which points into the patient's gluteal cleft, thereby avoiding overlaying the gluteal muscles, the two individually energisable segments being configured to be spaced at the midline and overlying at least the upper sacrum and being configured to be located to an area superior to the gluteal cleft in order to minimise overlap with the gluteal muscles such that the multifidus are stimulated, the height of the first electrode is limited such that it extends between and covers at least the fifth lumbar vertebra and the upper sacrum of the patient such that current is less likely to recruit large amounts of erector spinae muscle, and the width of the first electrode approximates the width of the multifidus and the vertebra, wherein the area of the first electrode is less than half the area of either second or third electrode to ensure the current density at multifidus is higher than at the second and third electrodes during the second group of muscular stimulation current pulses.

* * * * *